(12) United States Patent
Wysocki et al.

(10) Patent No.: US 9,025,163 B2
(45) Date of Patent: May 5, 2015

(54) CHIRP MODULATION-BASED DETECTION OF CHIRPED LASER MOLECULAR DISPERSION SPECTRA

(75) Inventors: Gerard Wysocki, Princeton, NJ (US); Michal Nikodem, Princeton, NJ (US)

(73) Assignee: The Trustess of Princeton University, Princeton, NJ (US)

( * ) Notice: Subject to any disclaimer, the term of this patent is extended or adjusted under 35 U.S.C. 154(b) by 251 days.

(21) Appl. No.: 13/453,499

(22) Filed: Apr. 23, 2012

(65) Prior Publication Data

US 2012/0268746 A1 Oct. 25, 2012

Related U.S. Application Data

(60) Provisional application No. 61/478,413, filed on Apr. 22, 2011.

(51) Int. Cl.
*G01N 21/41* (2006.01)
*G01N 21/45* (2006.01)

(52) U.S. Cl.
CPC .......... *G01N 21/45* (2013.01); *G01N 2021/451* (2013.01)

(58) Field of Classification Search
CPC ... G01B 9/02003; G01B 9/02007; G01J 3/45; G01J 9/04; G01N 21/45; G01N 21/455
USPC .......................................... 356/451, 517, 518
See application file for complete search history.

(56) References Cited

U.S. PATENT DOCUMENTS

| | | | |
|---|---|---|---|
| 4,847,512 A | | 7/1989 | Seta |
| 5,764,362 A | * | 6/1998 | Hill et al. ...................... 356/487 |
| 7,483,143 B2 | * | 1/2009 | Sanders et al. ................ 356/454 |
| 8,699,013 B2 | * | 4/2014 | Ogawa ......................... 356/73.1 |
| 2002/0140946 A1 | * | 10/2002 | Groot et al. ................... 356/517 |
| 2005/0012934 A1 | * | 1/2005 | Szafraniec .................... 356/484 |

(Continued)

FOREIGN PATENT DOCUMENTS

EP 0 920 599 A1 6/1999
EP 1 058 813 A1 12/2000
(Continued)

OTHER PUBLICATIONS

Wysocki et al., "Molecular dispersion spectroscopy for chemical sensing using chirped mid-infrared quantum cascade laser" vol. 18, No. 25 / Optics Express, pp. 26123-26140, Dec. 6, 2010.
Moschella et al., "Resonant, heterodyne laser interferometer for state density measurements in atoms and ions", Review of Scientific Instruments, vol. 77, No. 093108-1, 2006.
(Continued)

*Primary Examiner* — Tarifur Chowdhury
*Assistant Examiner* — Jonathon Cook
(74) *Attorney, Agent, or Firm* — Maegher Emanuel Laks Goldberg & Liao, LLP

(57) ABSTRACT

An apparatus and method for detecting refractive index variations in a sample is disclosed. The apparatus includes a multi frequency laser source configured to generate a mixed laser beam having at least two optical frequencies. A sinusoidal function generator is configured to modulate the optical frequencies to generate a chirp-modulated mixed laser beam. The chirp-modulated mixed laser beam being configured to pass through the sample. A detector is configured to detect the chirp-modulated mixed beam. A signal processer is configured to process the detected chirp-modulated mixed beam to measure refractive index variations in the sample.

20 Claims, 6 Drawing Sheets

(56) References Cited

U.S. PATENT DOCUMENTS

2009/0208202 A1* 8/2009 Lazaro Villa et al. ........... 398/16
2010/0245835 A1* 9/2010 Bennett .......................... 356/477
2012/0274929 A1   11/2012 Weidmann et al.

FOREIGN PATENT DOCUMENTS

JP    11-14544 A    1/1999
WO   WO 98/08047 A1   2/1998

OTHER PUBLICATIONS

Schwarze et al., "Method for obtaining gas concentration with a phase-based metrology system", Applied Optics, XP002621558, vol. 37, No. 18, pp. 3942-3947, Jun. 20, 1998.

Taslakov et al., "Open path atmospheric spectroscopy using room temperature operated pulsed quantum cascade laser", Spectrochimica Acta. Part A, XP025176687, vol. 63, No. 5, pp. 1002-1008, Apr. 1, 2006.

* cited by examiner

CHIRP MODULATION-BASED DETECTION OF CHIRPED LASER MOLECULAR DISPERSION SPECTRA

CROSS-REFERENCE TO PRIOR FILED APPLICATION

This application claims priority to earlier filed U.S. provisional patent application No. 61/478,413 filed on Apr. 22, 2011, which is herein incorporated by reference in its entirety.

GOVERNMENT RIGHTS IN THIS INVENTION

This invention was made with government support under Grant #CMMI-0954897 awarded by the National Science Foundation. The government has certain rights in this invention.

FIELD OF THE INVENTION

The present disclosure generally relates to chirp modulation based detection of chirped laser molecular dispersion spectra. The present disclosure also relates to spectroscopic applications in which continuous monitoring of the molecule concentration is needed. The present disclosure further relates to single point extractive sensing systems as well as open path remote sensors based on chirped laser dispersion spectroscopy.

BACKGROUND

Direct Chirped Laser Dispersion Spectroscopy (CLaDS) makes data analysis simple and straightforward, e.g. it enables fitting the dispersion profile using spectral databases (detailed description of CLaDS can be found in G. Wysocki and D. Weidmann, "Molecular dispersion spectroscopy for chemical sensing using chirped midinfrared quantum cascade laser," Opt. Express, vol. 18, pp. 26123-26140, 2010—incorporated herein in its entirety). Unfortunately, it has also important drawbacks. One is related to the frequency demodulation noise that contributes significantly to the total noise in CLaDS. Due to quadratic dependence of the frequency demodulation noise with the acquisition bandwidth a trade-off between noise level and data sampling needs to be made. Second drawback is the presence of a residual baseline in the measured spectrum. The conventional CLaDS is baseline-free as long as frequency-shifted beams that are responsible for CLaDS signal generation travel the same distance ($\Delta L=0$). In practice, however, $\Delta L \neq 0$, unless some additional opto-mechanical stabilization is used. For the typical chirp rates being between $10^{14}$ and $10^{15}$ Hz/s the path difference of only $\Delta L=1$ mm will result in the baseline level in the range of 50 to 500 Hz, whereas typical signal amplitude for the trace-gas sensing varies from tens of Hz to several tens of kHz, depending on the target molecular transition, molecular concentration, optical path length within the sample etc. Moreover, when the triangular modulation is used the resulting frequency chirp is not linear, thus the correct subtraction of the baseline requires fitting using higher order polynomials. Both issues can be minimized or eliminated when CLaDS signal is extracted using a Chirp Modulation (CM-CLaDS) scheme.

The present disclosure relates to chirped laser dispersion spectroscopy (CLaDS) systems. By applying the process disclosed herein, the baseline in the dispersion measurement may be reduced and measurement is made more immune to opto-mechanical fluctuations. In addition, by applying the process disclosed herein, the noise level may be reduced and signal to noise ratio can be improved compared to the conventional method. The process disclosed herein may be used in spectroscopic applications in which continuous monitoring of the molecule concentration is needed. The method may be used with single point extractive sensing systems as well as with open path remote sensors based on CLaDS.

SUMMARY OF THE INVENTION

Figure 1:
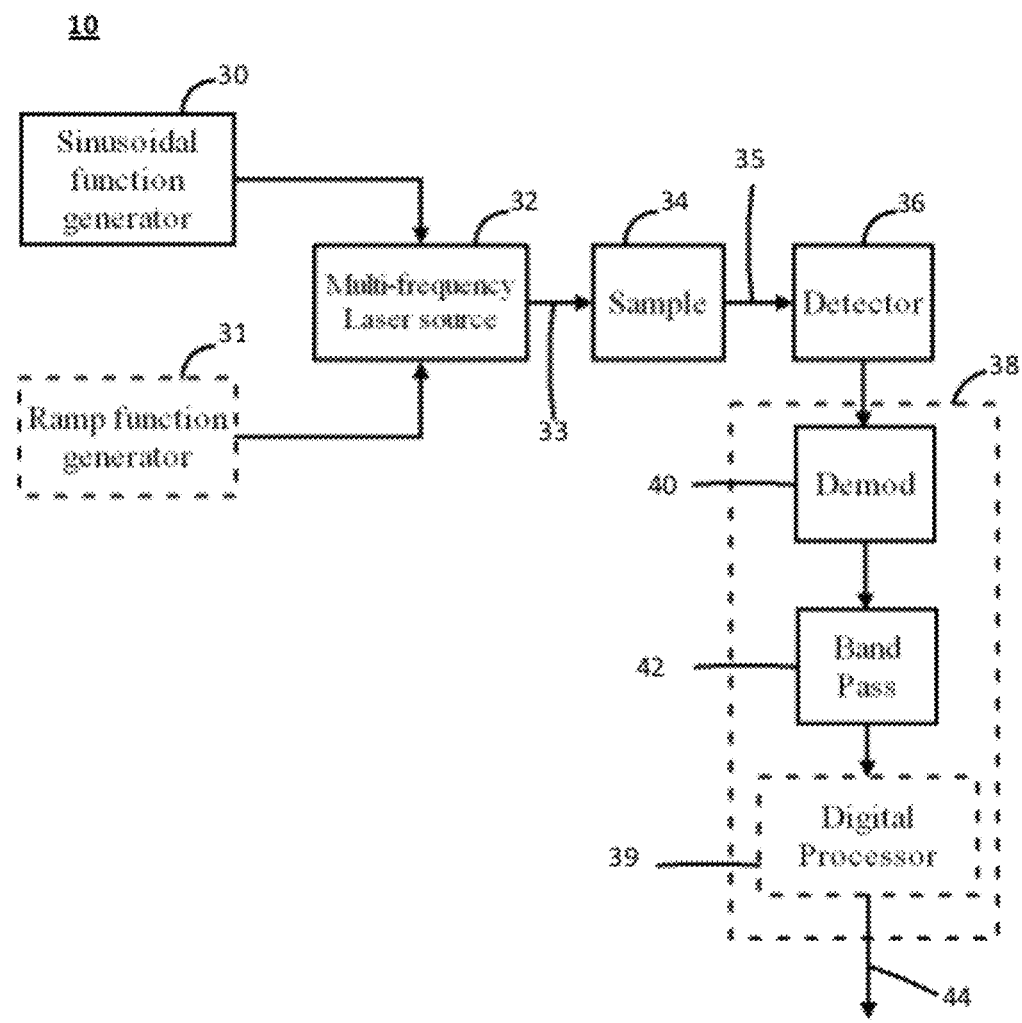
FIG. 1 is block diagram of an apparatus configured for detecting refractive index changes in a sample.

An apparatus and method for detecting refractive index variations in a sample is disclosed. The apparatus includes a multi-frequency laser source configured to generate a laser beam composed of multiple waves at different optical frequencies (mixed laser beam). A sinusoidal function generator is configured to modulate optical frequencies to generate a chirp-modulated mixed laser beam. The chirp-modulated mixed laser beam being configured to pass through the sample. A detector is configured to detect the chirp-modulated mixed beam. A signal processer is configured to process the detected chirp-modulated mixed beam to measure refractive index variations in the sample.

The signal processer may include a demodulator configured to demodulate the detected chirp-modulated mixed beam to generate a demodulated output. The signal processer may also include a band pass filter configured to transmit only a fundamental frequency of the demodulated output or a plurality of harmonics from the demodulated output. The apparatus may further include a ramp function generator configured to scan the multi frequency laser source over a range of frequencies. The ramp function generator may have a frequency in the 0.1 mHz to 100 Hz range.

The detector may be a square law detector or other non-linear optical element configured to generate beat signals between the optical frequencies of the laser source. The signal processer may be configured to analyze beat signals. The signal processor may be configured to measure at least one of frequency and a phase change in the beat signal. The sinusoidal function generator may have a frequency in the 10 kHz to 1 MHz range. The multi frequency laser source may include a semiconductor laser. The multi frequency laser source may include a laser, an optical modulator and/or beam combiner.

A method for detecting refractive index variations in a sample is also disclosed. The method may include, generating a mixed laser beam having at least two optical frequencies; sinusoidally modulating optical frequencies to generate a chirp-modulated mixed laser beam, the chirp-modulated mixed laser beam being configured to pass through the sample; detecting the mixed beam; and signal processing the detected chirp-modulated mixed beam to measure refractive index variations in the sample.

Signal processing the detected chirp-modulated mixed beam may include demodulating the detected chirp-modulated mixed beam to generate a demodulated output. Signal processing the detected chirp-modulated mixed beam may also include band pass filtering the demodulated output to transmit only a fundamental frequency of the demodulated output or a plurality of harmonics from the demodulated output. The method may also include scanning the multi frequency laser source over a range of frequencies (the multi frequency laser source may be scanned in frequency within the 100 MHz to 100 GHz range) or active (or passive) locking of the frequency of the laser source to the center of the measured dispersion profile.

Signal processing the detected chirp-modulated mixed beam may include analyzing a beat signal. Signal processing the detected chirp-modulated mixed beam may also include measuring at least one of a frequency and phase change in the beat signal. The optical frequency of the mixed laser beam may be sinusoidally modulated with a frequency in the 10 kHz to 1 MHz range. The mixed laser beam may be generated using a semiconductor laser. The mixed laser beam may be generated using a laser, an optical modulator and/or beam combiner.

DETAILED DESCRIPTION OF THE INVENTION

The present disclosure generally relates to chirp modulation based detection of chirped laser molecular dispersion spectra. FIG. 1 is a block diagram of an apparatus 10 configured for detecting refractive index changes when light passes through a sample due to the presence of molecules in the sample. The apparatus 10 includes a sinusoidal function generator 30 having a modulation frequency f. The sinusoidal function generator 30 is coupled to a multi frequency laser source 32. The multi frequency laser source 32 is configured to generate a mixed laser beam having two or more frequencies (mixed laser beam). In a typical configuration, the frequencies that generate the dispersion signal may differ by $\Omega$ of 10 MHz to 10 GHz. This will result in the generation of a beat note at $\Omega$ as discussed in more detail below. It should be understood that the selection of the laser beam center frequencies and beat note frequency will depend on the frequencies that are relevant to specific molecule(s) that are sought to be measured.

The multi frequency laser source 32 is configured to modulate the laser frequencies at the modulation frequency f, generating a chirp-modulated mixed laser beam at the output 33 of the multi frequency laser source 32. The chirp-modulated mixed laser beam is configured to pass through the sample 34 as shown by reference number 35. Detector 36 is configured to detect the chirp-modulated mixed beam 35. The dispersion (refractive index change) in the sample has different effect on the propagation time of the wave components of the multi frequency laser source 32. As the mixed laser beam 35 is frequency chirped, the difference in propagation times for different wave components results in the change of frequency of the measured heterodyne beatnote. Signal processor 38 is configured to process the detected chirp-modulated mixed beam 35 to measure refractive index variations in the sample 34 and generate output signal 42. The output signal 44 is generally a heterodyne beatnote that may be analyzed to detect frequency changes in the beat signal which correspond to changes in the refractive index of the sample.

The multi frequency laser source 32 may be implemented in a variety of configurations including a direct generation of two or more frequencies from a laser or by using single-frequency laser source and a single side band (SSB) modulator, acousto-optical frequency shifter, electro-optical amplitude modulator, through direct modulation of the laser parameters, or combination of those. Signal processor 38 generally includes a demodulator 40 configured to demodulate the detected chirp-modulated mixed beam to generate a demodulated output (heterodyne beatnote). Signal processer 38 also includes a band pass filter configured to so that only specific harmonics of the fundamental modulation frequency f are analyzed. Spectroscopic information is encoded in the parameters (amplitude and phase) of the harmonics of the frequency demodulated heterodyne beatnote and, depending on implementation, can be obtained directly at the output of the band-pass filter 42 or can be retrieved after analog or digital processing of the signal after band-pass filter 42. Demodulator 40 and band pass filter 42 may be implemented using a variety of analog and/or digital techniques as is known in the art. Signal processor 38 may also include a digital processor 39 configured to implement the demodulator 40 and/or band pass filter 42. Digital processor 39 may also be configured to retrieve spectroscopic information after band-pass filtering and to record and fit measured refractive index changes using a spectroscopic database (if ramp function generator 31 is used to scan multi frequency laser source 32) or to retrieve information on target analyte based on an instrument calibration scaling factor (if frequency of the multi frequency laser source 32 is locked at the center of the measured dispersion profile). Useful information is provided by the parameters (amplitude and phase) of the 2nd harmonic (baseline-free dispersion spectrum) and the 1st harmonic of the signal that is obtained after demodulation of the heterodyne beatnote as discussed below.

Apparatus 10 may also include a ramp function generator 31, configured to scan the multi frequency laser source 32 over a range of frequencies. For example, the multi frequency laser source 32 may be configured to generate optical frequencies in the 50-400 THz range. The sinusoidal function generator 30 may be configured with a frequency in the 10 kHz-1 MHz range. In general, as the frequency of the sinusoidal function generator 30 is increased, the output at the detector 36 also increases. The ramp function generator 31 may be configured with a relatively low frequency such as 1 Hz. The ramp signal is generally used to scan the laser center frequencies over a range from approximately 100 MHz to 100 GHz. This allows for generation of more detailed spectral information that can be used for retrieving not only concentration but also other sample parameters such as pressure or temperature (see FIG. 5 discussed below). If ramp signal is not applied by using well established active optical frequency locking methods frequency of the laser source 32 may be locked to the maximum of the 2nd harmonic CM-CLaDS signal in order to retrieve information on the sample based on the signal maximum only (for example to monitor concentration or temperature).

Figure 2:
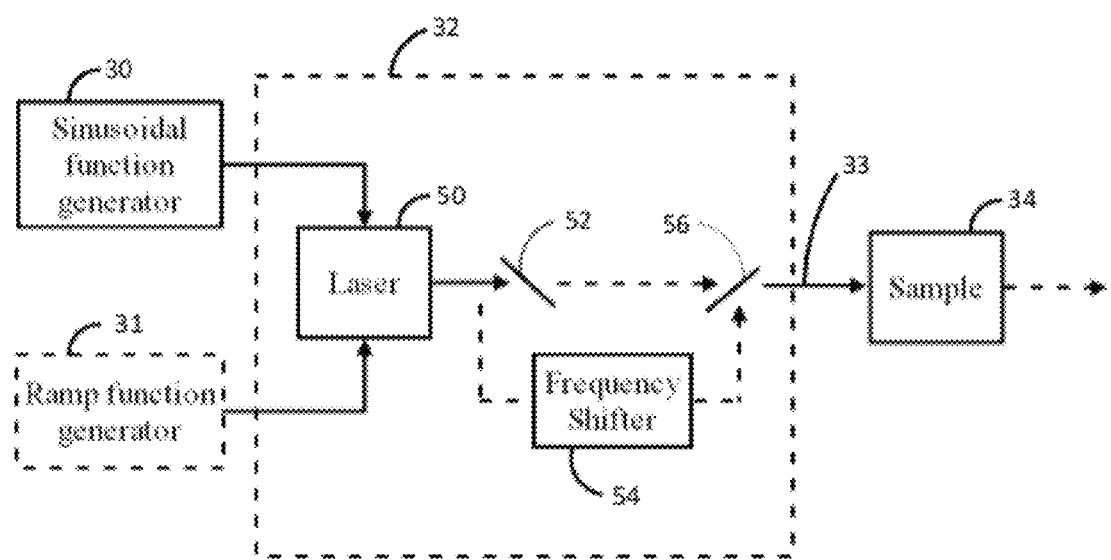
FIG. 2 is a block diagram of a dual frequency laser source implemented using a frequency shifter and beam combiner.

FIG. 2 is a block diagram of an example of multi frequency laser source 32 implemented using a frequency shifter and beam combiner. In this example, the multi frequency laser source 32 generates two frequencies. It includes a laser 50 configured to generate a single frequency output. A sinusoidal function generator 30 having a modulation frequency f is used to modulate the laser as discussed above. The modulated laser output is directed into a beam splitter 52 that splits the laser output into two beams. A frequency shifter 54 is introduced into the path of one of the two beams (as a frequency shifter one can use, for example, acousto-optical frequency shifter or electro-optical modulator). A beam combiner 56 combines the two beams to generate a chirp-modulated mixed laser beam at the output 33 of the multi frequency laser source 32. A ramp function generator 31 may also be used to scan the beam from multi frequency laser source 32 over a range of frequencies as discussed above.

Figure 3:
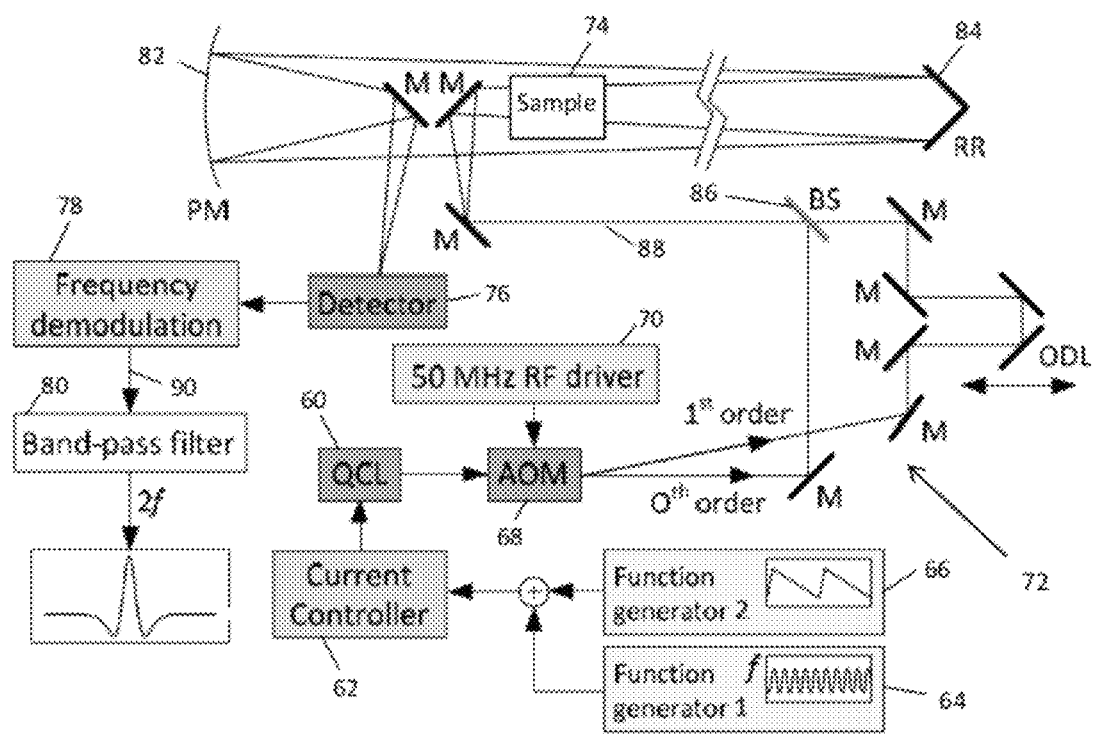
FIG. 3 is a block diagram of a CM-CLaDS system.

FIG. 3 is a block diagram of one example of a CM-CLaDS embodiment. In this example, a quantum cascade laser (QCL) 60 is used as a laser source. It should be understood that a variety of lasers, including semiconductor lasers such as a QCL, may be used without departing from the scope of this disclosure. The QCL frequency is modulated by modulating its injection current via current controller 62 and an external sinusoidal waveform from Function generator 1 (reference number 64). The output of the QCL 60 is coupled to an acousto-optic modulator (AOM) 68. An RF driver 70 having a frequency $\Omega=50$ MHz is coupled to the AOM 68. The AOM 68 generates first and second laser beams having center frequencies that differ in frequency by 50 MHz. An optical delay line 72 is used to compensate for small unbalances in the interferometer. The first and second laser beams are combined via beam splitter 86 resulting in a chirp-modulated mixed beam 88 that is directed through a sample 74. In this example, the chirp-modulated mixed beam 88 is directed through a light path having a remote detection configuration including a retroreflector 84 and parabolic mirror 82. It should be understood that a variety of optical configurations may be used for directing the chirp-modulated mixed beam through the sample one or more times without departing from the scope of this disclosure. It should also be understood that the sample may be placed in a variety of locations in the light path without departing from the scope of this disclosure.

The signal 90 that is recovered after frequency demodulation of the heterodyne beatnote is post-processed in order to analyze its in-phase and quadrature components at the harmonics of the modulation frequency. An additional ramp signal from Function generator 2 (66) may be used to scan the laser wavelength or the laser frequency can be locked to the peak of the molecular transition of interest for continuous concentration monitoring.

Analysis of the signal at the higher (>1st) harmonics of the modulation frequency helps to overcome both drawbacks of the direct detection scheme. It enables reduction of the acquisition bandwidth which leads to frequency demodulation noise reduction and helps to increase the signal-to-noise ratio (SNR), as well as eliminates baseline due to imbalance within the interferometer. In CM-CLaDS only 1st harmonic is affected by the unbalance of the interferometer arms. Therefore the 2nd harmonic signal can be used for continuous concentration monitoring since, in theory, it is baseline-free.

Figure 4:
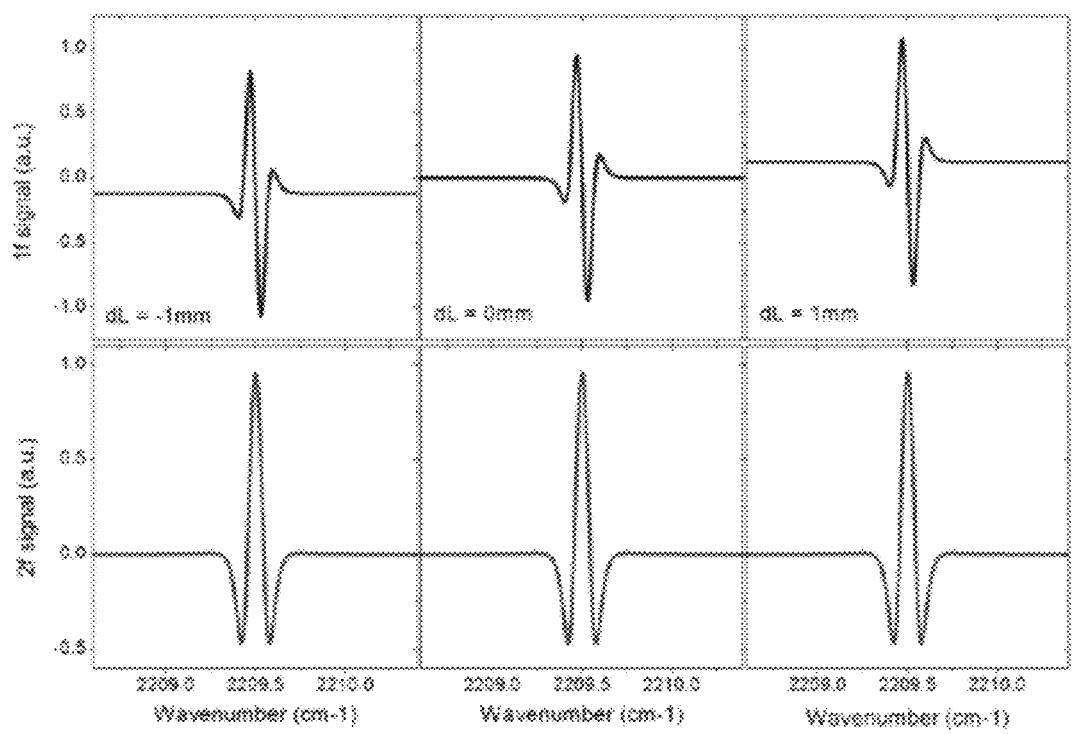
FIG. 4 is a graph showing amplitude normalized CM-CLaDS signals calculated for $N_2O$ transition and different unbalance of the interferometer.

FIG. 4 is a graph showing amplitude normalized CM-CLaDS signals calculated for $N_2O$ transition and different unbalance of the interferometer. 1f and 2f signals are shown. Calculation is made for ambient pressure, $N_2O$ concentration of 320 ppb, 10 m optical path, 50 MHz frequency spacing, maximal chirp rate of 1 MHz/ns, and modulation depth of 1.5 GHz. For 1f spectra small unbalance of the interferometer creates baseline. On the other hand, 2f signals are baseline-free thus the output spectrum does not require any baseline correction and amplitude of 2f signal is proportional to target analyte concentration. At the same time, with small unbalance of the interferometer (which can be precisely controlled with optical delay line 72), 1f signal enables determination of the instantaneous chirp rate of the laser, which for most lasers might vary while the wavelength is tuned. Since CLaDS signal is chirp rate dependent, this capability provides a convenient way for proper real time CM-CLaDS signal calibration with no need for an additional instrumentation or measurements.

The disclosed approach involves two additional steps in comparison to the conventional CLaDS. The first step is related to the way the laser frequency is chirped. In conventional CLaDS laser frequency is chirped linearly across the entire target spectral range. In CM-CLaDS the laser chirp is modulated sinusoidally (in semiconductor laser it can be obtained through laser current modulation) with the frequency f. The laser frequency modulation depth should be comparable to the linewidth of the molecular transition (optimal modulation depth depends on the linewidth and the frequency spacing $\Omega$ provided by the multi frequency laser source 32). The second step of the process is band-pass filtering of the signal obtained through frequency demodulation of the heterodyne beatnote around frequency $\Omega$. The signal recovered after frequency demodulation is filtered so that only specific harmonics of the fundamental modulation frequency f are analyzed. The most useful information is provided by the 2nd harmonic (baseline-free dispersion spectrum) and the 1st harmonic (if $\Delta L \neq 0$ it can provide information about the chirp rate and the modulation depth). All harmonics above the $2^{nd}$ harmonic may also contain useful information.

The CM-CLaDS configuration was verified experimentally. Remote open-path sensing of nitrous oxide ($N_2O$) was carried out in the laboratory conditions. Approximately 315 ppb concentration of $N_2O$ in the laboratory air was determined based on the standard absorption measurement. The round-trip total optical path of 50 m between CLaDS setup (as shown in FIG. 3) and retroreflector was set-up in the lab. The modulation frequency and acquisition bandwidth were set to 100 kHz and 800 kHz, respectively. LabView software was used to access the signal demodulated by the RF spectrum analyzer and digitally filter the demodulated signal in order to recover the in-phase and quadrature component (a lock-in amplifier can also be used for this purpose). An additional slow ramp signal (Function generator 2 (66)) was used to scan the laser wavelength across more than 2 cm-1 allowing for observation of three $N_2O$ transitions (2209.5, 2210.5 and 2211.4 cm-1).

Figure 5:
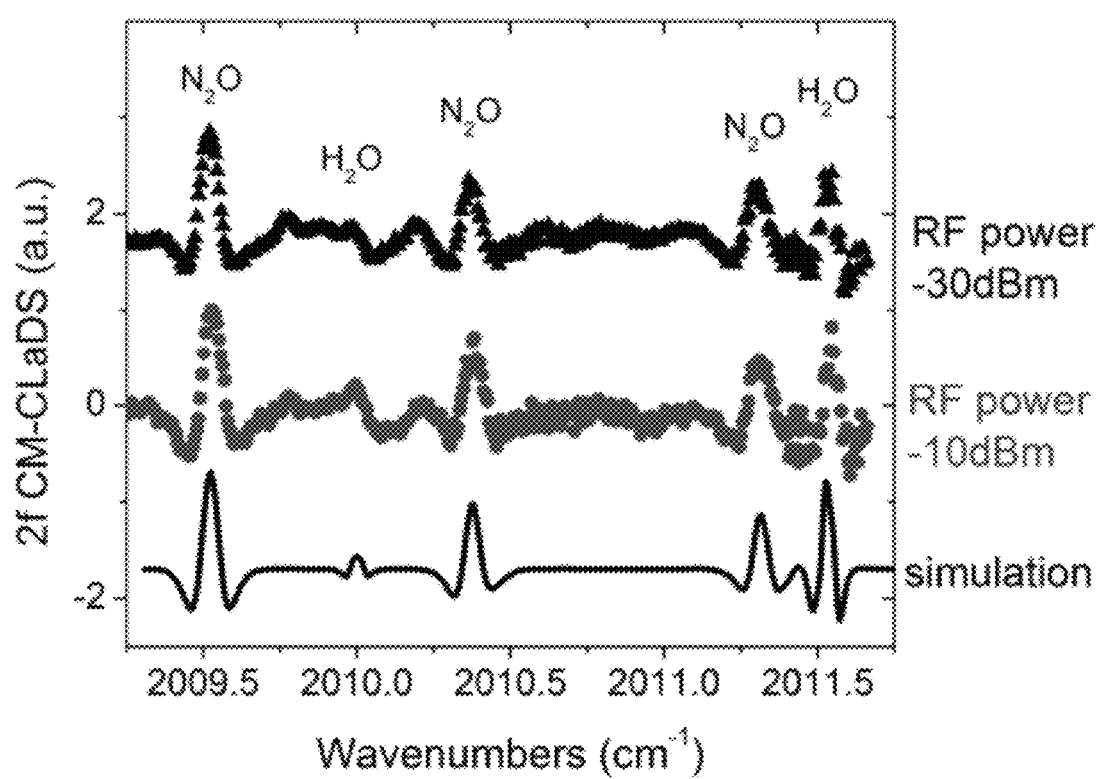
FIG. 5 is a graph showing dispersion spectra recorded using CM-CLaDS with 2f detection scheme (top) and the simulation using the HITRAN database (bottom)

FIG. 5 is a graph showing dispersion spectra recorded using CM-CLaDS with 2f detection scheme (the first and the second spectrum from the top) and the simulation using HITRAN database (bottom). Despite being recorded at different powers of the heterodyne beatnote, two measured signals are almost identical (which proves immunity of CM-CLaDS to optical power variations). The laser wavelength was scanned by a slow change of the injection current, from the threshold level (100 mA) to the roll-off of the LIV curve (170 mA). The laser frequency was chirped using additional 100 kHz sinusoidal signal with 4 mA peak-to-peak amplitude. As a result, the sinusoidal chirp of the laser optical frequency was obtained and, after filtering, the amplitude of the 2f component of the CLaDS signal was recovered. Two measured spectra as shown in FIG. 5 agree well with the simulated spectrum in the same spectral range. There was a $\Delta L=1$ mm path difference purposely set-up between two interferometer arms. Although this difference would cause baseline effect in a conventional CLaDS both spectra acquired using CM-CLaDS are baseline-free. Moreover, despite a 20 dB decrease in RF signal power they have almost identical amplitude and SNR, which proves the immunity of CLaDS to optical power variations. This property, so important in open-path sensing, was observed in direct-CLaDS and is still valid for CM-CLaDS.

Figure 6:
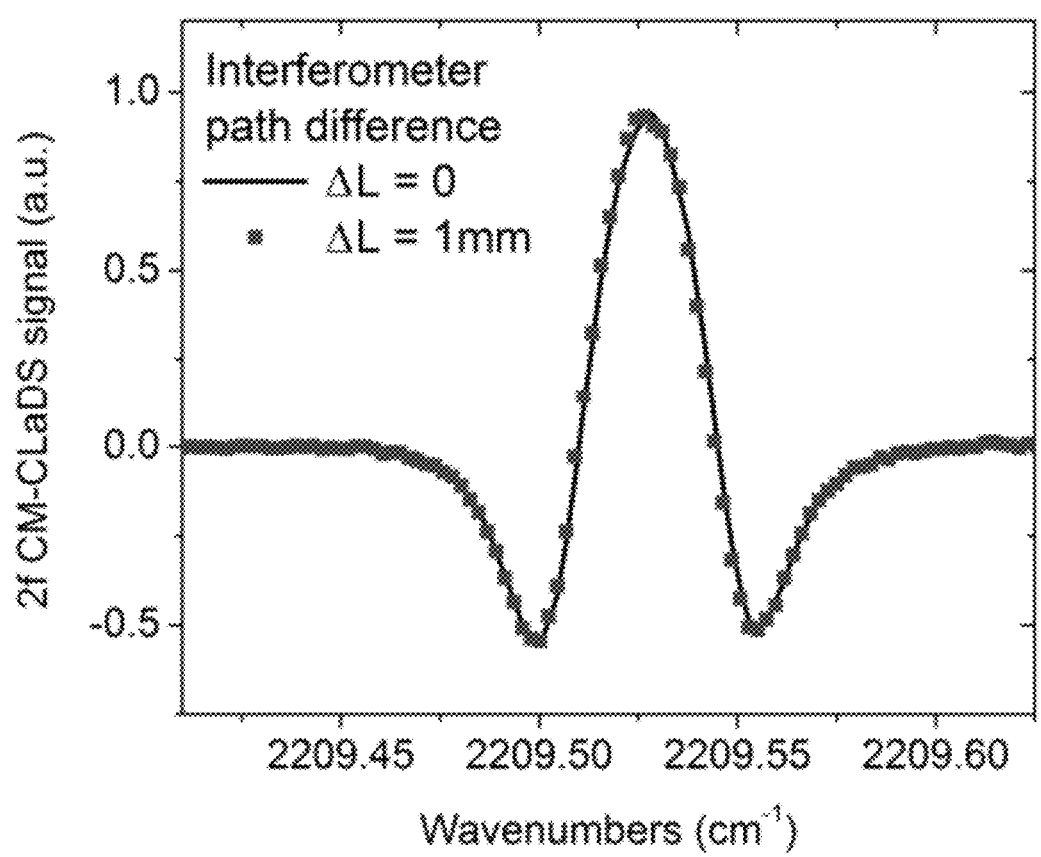
FIG. 6 is a graph showing the 2f signal recorded when the laser frequency was tuned across the $N_2O$ transition at 2209.52 cm-1, measured for different values of $\Delta L$.

To verify if the unbalance of the interferometer does not generate the baseline in the 2f spectrum, the 2nd harmonic signal was measured for two different values of ΔL. The path difference was precisely changed using optical delay line (ODL) 72 from 0 mm to 1 mm. FIG. 6 is a graph showing the 2f signals recorded when the laser frequency was tuned across the $N_2O$ transition at 2209.52 cm-1, measured for two different values of ΔL. The 2f signal remains stable despite ΔL change is relatively large. The sensitivity improvement was verified by comparing the detection limit of conventional CLaDS with the new CM-CLaDS. In the disclosed configuration, CM-CLaDS results in an increase in the sensitivity by a factor of ~3 (the improvement is limited only by optical fringe noise). If optical fringes are suppressed, in conventional CLaDS the SNR is limited mainly by the FM-demodulation noise. In CM-CLaDS the demodulation noise can be strongly reduced by reduction of the demodulation bandwidth. Because in prototype system optical fringes were dominant it was not possible to take full advantage of the acquisition bandwidth reduction that CM-CLaDS provides. It is expected that after elimination of the parasitic optical fringes (e.g. by using better antireflective coatings on the AOM facets) the detection limit improvement in CM-CLaDS will be at the level of 10 to 100 times if compared to the conventional CLaDS detection scheme.

This process may be applied to the setup that is designed to perform direct chirped laser dispersion spectroscopy, which is described in G. Wysocki and D. Weidmann, "Molecular dispersion spectroscopy for chemical sensing using chirped midinfrared quantum cascade laser," Opt. Express, vol. 18, pp. 26123-26140, 2010, to improve its performance. The method can be used to enhance sensing capabilities of existing laser spectroscopic systems by introducing frequency chirping of the laser source and CLaDS detection of the photodetected signals. CM-CLaDS helps to overcome drawbacks of the direct detection scheme, while keeping all advantages of the conventional CLaDS (e.g. immunity to optical power variations and large dynamic range of the measurement). This configuration may be easily implemented to the conventional CLaDS systems or even conventional laser absorption spectrometers without modifications to the optomechanical design.

It should be understood that many variations of the measurement system are possible based on the disclosure herein. Although features and elements are described above in particular combinations, each feature or element can be used alone without the other features and elements or in various combinations with or without other features and elements. The methods or flow charts provided herein may be implemented in a computer program, software, or firmware incorporated in a computer-readable storage medium for execution by a general purpose computer or a processor. Examples of computer-readable storage mediums include a read only memory (ROM), a random access memory (RAM), a register, cache memory, semiconductor memory devices, magnetic media such as internal hard disks, SSDs and removable disks, magneto-optical media, and optical media such as CD-ROM disks, and digital versatile disks (DVDs).

Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors may be manufactured by configuring a manufacturing process using the results of processed hardware description language (HDL) instructions and other intermediary data including netlists (such instructions capable of being stored on a computer readable media). The results of such processing may be maskworks that are then used in a semiconductor manufacturing process to manufacture a processor which implements aspects of the present invention.

What is claimed is:

1. An apparatus for detecting refractive index variations in a sample, the apparatus comprising:
    a multi frequency laser source configured to generate a mixed laser beam having at least two optical frequencies;
    a sinusoidal function generator configured to modulate the optical frequencies to generate a chirp-modulated mixed laser beam, the chirp-modulated mixed laser beam being configured to pass through the sample and generate a beat signal with frequency changes that correspond to changes in the refractive index of the sample;
    a detector configured to detect the frequency changes in the beat signal of the chirp-modulated mixed beam; and
    a signal processer configured to process the detected frequency changes in the beat signal of the chirp-modulated mixed beam to measure refractive index variations in the sample.

2. The apparatus of claim 1 wherein the signal processer includes a demodulator configured to demodulate the detected chirp-modulated mixed beam to generate a demodulated output.

3. The apparatus of claim 1 wherein the signal processer includes a band pass filter configured to transmit only a fundamental frequency of the demodulated output or a plurality of harmonics from the demodulated output.

4. The apparatus of claim 1 further comprising a ramp function generator configured to scan the multi frequency laser source over a range of frequencies.

5. The apparatus of claim 4 wherein the ramp function generator has a frequency in the 0.1 mHz to 100 Hz range.

6. The apparatus of claim 1 wherein the detector is a square law detector or other non-linear optical element configured to generate beat signals between the optical frequencies of the laser source.

7. The apparatus of claim 1 wherein the signal processor is configured to measure at least one of frequency and a phase change in the beat signal.

8. The apparatus of claim 1 wherein the sinusoidal function generator has a frequency in the 10 kHz to 1 MHz range.

9. The apparatus of claim 1 wherein the multi frequency laser source includes a semiconductor laser.

10. The apparatus of claim 1 wherein the multi frequency laser source includes a laser and at least one of an optical modulator and a beam combiner.

11. Apparatus for detecting refractive index variations in a sample, the apparatus comprising:
    a multi frequency laser source configured to generate a mixed laser beam having at least two optical frequencies;
    a sinusoidal function generator configured to modulate the optical frequencies to generate a chirp-modulated mixed laser beam, the chirp-modulated mixed laser beam being configured to pass through the sample and generate a beat signal with frequency changes that correspond to changes in the refractive index of the sample;
    a detector configured to detect the frequency changes in the beat signal of the chirp-modulated mixed beam;

a demodulator configured to demodulate the detected chirp-modulated mixed beam to generate a demodulated output; and a band pass filter configured to transmit only a fundamental frequency of the demodulated output or a plurality of harmonics from the demodulated output.

12. A method for detecting refractive index variations in a sample, the method comprising:

generating a mixed laser beam having at least two optical frequencies;

sinusoidally modulating the optical frequencies to generate a chirp-modulated mixed laser beam, the chirp-modulated mixed laser beam being configured to pass through the sample and generating a beat signal with frequency changes that correspond to changes in the refractive index of the sample and generate a beat signal with frequency changes that correspond to changes in the refractive index of the sample;

detecting the frequency changes in the beat signal of the chirp-modulated mixed beam; and signal processing the detected frequency changes in the beat signal of the chirp-modulated mixed beam to measure refractive index variations in the sample.

13. The method of claim 12 wherein signal processing the detected chirp-modulated mixed beam includes demodulating the detected chirp-modulated mixed beam to generate a demodulated output.

14. The method of claim 12 wherein signal processing the detected chirp-modulated mixed beam includes band pass filtering the demodulated output to transmit only a fundamental frequency of the demodulated output or a plurality of harmonics from the demodulated output.

15. The method of claim 12 further comprising scanning the multi frequency laser source over a range of frequencies.

16. The method of claim 15 wherein the multi frequency laser source is scanned in frequency within the 100 MHz to 100 GHz range.

17. The method of claim 12 wherein signal processing the detected chirp-modulated mixed beam includes measuring at least one of a frequency and phase change in the beat signal.

18. The method of claim 12 wherein the optical frequency of the mixed laser beam is sinusoidally modulated with a frequency in the 10 kHz to 1 MHz range.

19. The method of claim 12 wherein the mixed laser beam is generated using a semiconductor laser.

20. The method of claim 12 wherein the mixed laser beam is generated using a laser, and at least one of an optical modulator and a beam combiner.

\* \* \* \* \*